United States Patent [19]

Shander et al.

[11] Patent Number: 5,728,736
[45] Date of Patent: Mar. 17, 1998

[54] REDUCTION OF HAIR GROWTH

[76] Inventors: Douglas Shander, 16112 Howard Landing Dr., Gaithersburg, Md. 20878; Margaret Funkhouser, 10307 Hickory Creek Ct., Great Falls, Va. 22066; James Henry, 6776 Wood Duck Ct., Frederick, Md. 21701; Gurpreet Ahluwalia, 8632 Stableview Ct., Gaithersburg, Md. 20852

[21] Appl. No.: 564,491

[22] Filed: Nov. 29, 1995

[51] Int. Cl.$^6$ .................................................. A61K 31/195

[52] U.S. Cl. .......................... 514/561; 514/562; 514/564; 514/565; 514/638

[58] Field of Search ................................. 514/561, 562, 514/564, 565, 635

[56] References Cited

U.S. PATENT DOCUMENTS

| | | |
|---|---|---|
| 3,426,137 | 2/1969 | Philpitt . |
| 4,039,669 | 8/1977 | Beyler et al. . |
| 4,139,638 | 2/1979 | Neri et al. . |
| 4,161,540 | 7/1979 | Neri et al. . |
| 4,191,775 | 3/1980 | Glen . |
| 4,269,831 | 5/1981 | Ferrari et al. . |
| 4,344,941 | 8/1982 | Wiechert et al. . |
| 4,370,315 | 1/1983 | Greff et al. . |
| 4,439,432 | 3/1984 | Peat . |
| 4,508,714 | 4/1985 | Cecic et al. . |
| 4,517,175 | 5/1985 | Iwabuchi et al. . |
| 4,720,489 | 1/1988 | Shander . |
| 4,885,289 | 12/1989 | Breuer et al. . |
| 4,935,231 | 6/1990 | Pigiet . |
| 5,095,007 | 3/1992 | Ahluwalia . |
| 5,096,911 | 3/1992 | Ahluwalia et al. . |
| 5,132,293 | 7/1992 | Shander et al. . |
| 5,143,925 | 9/1992 | Shander et al. . |
| 5,189,212 | 2/1993 | Ruenitz . |
| 5,271,942 | 12/1993 | Heverhagen . |
| 5,300,284 | 4/1994 | Wiechers et al. . |
| 5,364,885 | 11/1994 | Ahluwalia et al. . |
| 5,411,991 | 5/1995 | Shander et al. . |
| 5,455,234 | 10/1995 | Ahluwalia et al. . |
| 5,468,476 | 11/1995 | Ahluwalia et al. . |
| 5,474,763 | 12/1995 | Shander et al. . |
| 5,554,608 | 9/1996 | Ahluwalia et al. ................. 514/212 |

FOREIGN PATENT DOCUMENTS

| | | |
|---|---|---|
| 0 413 528 A1 | 2/1991 | European Pat. Off. . |
| 0 532 219 A2 | 3/1993 | European Pat. Off. . |
| 2 609 393 A1 | 7/1988 | France . |
| 1 458 349 | 12/1976 | United Kingdom . |

OTHER PUBLICATIONS

Pratzel et al., "Biochemistry of Free Amino Acids in the Stratum Corneum of Human Epidermis", *Arch. Dermtol. Res.*, vol. 259, No. 2, 1977.

Simpson et al., "The Effect of Topically Applied Progesterone on Sebum Excretion Rate", *British Journal of Dermatology*, 100:687–692 (1979).

Harmon et al., "12–O–Tetradecanoylphorbol–13–Acetate Inhibits Human Hair Follicle Growth and Hair Fiber . . . ", *SID Abstracts*, 102:533 (1994).

"Cochlear damage and increased threshold in alphadifluoromethylornithine (DFMO) treated guinea pigs"(abstract only).

Sato, "The Hair Cycle and Its Control Mechanism", *Biology and Disease of the Hair* pp. 3–13 (1975).

Goos et al., "An Improved Method for Evaluating Antiandrogens", *Arch. Dermatol. Res.*, 273:333–341 (1982).

Messenger, "The Control of Hair Growth: An Overview", *The Journal of Investigative Dermatology*, 101:4S–9S, supplement, (1993).

*Primary Examiner*—Rebecca Cook
*Attorney, Agent, or Firm*—Fish & Richardson P.C.

[57] ABSTRACT

Mammalian hair growth is reduced by applying to the skin a dermatologically acceptable composition including an inhibitor of arginase.

17 Claims, No Drawings

REDUCTION OF HAIR GROWTH

The invention relates to a method of reducing unwanted hair growth in mammals.

A main function of mammalian hair is to provide environmental protection. However, that function has largely been lost in humans, in whom hair is kept or removed from various parts of the body essentially for cosmetic reasons. For example, it is generally preferred to have hair on the scalp but not on the face.

Various procedures have been employed to remove unwanted hair, including shaving, electrolysis, depilatory creams or lotions, waxing, plucking, and therapeutic antiandrogens. These conventional procedures generally have drawbacks associated with them. Shaving, for instance, can cause nicks and cuts, and can leave a perception of an increase in the rate of hair regrowth. Shaving also can leave an undesirable stubble. Electrolysis, on the other hand, can keep a treated area free of hair for prolonged periods of time, but can be expensive, painful, and sometimes leaves scarring. Depilatory creams, though very effective, typically are not recommended for frequent use due to their high irritancy potential. Waxing and plucking can cause pain, discomfort, and poor removal of short hair. Finally, antiandrogens—which have been used to treat female hirsutism—can have unwanted side effects.

It has previously been disclosed that the rate and character of hair growth can be altered by applying to the skin inhibitors of certain enzymes. These inhibitors include inhibitors of 5-alpha reductase, ornithine decarboxylase, S-adenosylmethionine decarboxylase, gamma-glutamyl transpeptidase, and transglutaminase. See, for example, Breuer et al., U.S. Pat. No. 4,885,289; Shander, U.S. Pat. No. 4,720,489; Ahluwalia, U.S. Pat. No. 5,095,007; Ahluwalia et al., U.S. Pat. No. 5,096,911; Shander et al., U.S. Pat. No. 5,132,293; and Shander et al., U.S. Pat. No. 5,143,925.

Arginase (L-argine aminohydrolase EC 3.5.3.1) catalyzes the hydrolysis of L-arginine into ornithine and urea.

It has now been found that unwanted mammalian (including human) hair growth—particularly androgen-stimulated hair growth—can be reduced by applying to the skin a dermatologically acceptable composition including an inhibitor of arginase in an amount effective to reduce hair growth. The unwanted hair growth which is reduced may be normal hair growth, or hair growth that results from an abnormal or diseased condition.

Preferred inhibitors of arginase include alpha aminoisobutryic acid (Bedford et al., 1988 Proceedings of the Society for Experimental Biology and Medicine 188, 509–14); $N^{G}$-hydroxy-L-arginine (Daghigh et al., 1994 Biophysical Biochem. Res. Comm. 202, 174–80); 1-ethyl-3-(3-dimethylaminopropyl)-carbodiimide (Turkoglu et al., 1991 Int. J. Biochem. 23, 147–51); octopinen; N-tosyl-L-arginine; and N-p-tosyl-L-arginine methylester. The latter compound is converted in vivo to N-p-tosyl-L-arginine by tissue esterases. "Inhibitors", as used herein, include compounds which themselves inhibit arginase and compounds which in vivo convert to compounds that inhibit arginase. The preferred inhibitors are irreversible.

The inhibitor of arginase preferably is incorporated in a topical composition which includes a non-toxic dermatologically acceptable vehicle or carrier which is adapted to be spread upon the skin. Examples of suitable vehicles are acetone, alcohols, or a cream, lotion, or gel which can effectively deliver the active compound. One such vehicle is disclosed in co-pending application PCT/US 93/0506A. In addition, a penetration enhancer may be added to the vehicle to further enhance the effectiveness of the formulation.

The concentration of the inhibitor of arginase in the composition may be varied over a wide range up to a saturated solution, preferably from 0.1% to 30% by weight or even more; the reduction of hair growth generally increases as the amount of the inhibitor applied increases per unit area of skin. The maximum amount effectively applied is limited only by the rate at which the inhibitor penetrates the skin. Generally, the effective amounts range from 100 to 3000 micrograms or more per square centimeter of skin.

The composition should be topically applied to a selected area of the body from which it is desired to reduce hair growth. For example, the composition can be applied to the face, particularly to the beard area of the face, i.e., the cheek, neck, upper lip, and chin. The composition can also be applied to the legs, arms, torso or armpits. The composition is particularly suitable for reducing the growth of unwanted hair in women suffering from hirsutism or other conditions. In humans, the composition should be applied once or twice a day, or even more frequently, for at least three months to achieve a perceived reduction in hair growth. Reduction is hair growth is demonstrated when the frequency of hair removal (shaving, tweezing, depilatory use, waxing) is reduced, or the subject perceives less hair on the treated site, or quantitatively, when the weight of hair removed by shaving (i.e., hair mass) is reduced. Benefits of reduced hair removal frequency include convenience and less skin irritation.

Male intact Golden Syrian hamsters are considered acceptable models for human beard hair growth in that they display oval shaped flank organs, one of each side, each about 8 mm. in major diameter, which growth thick black and coarse hair similar to human beard hair. These organs produce hair in response to androgens in the hamster. To evaluate the effectiveness of a particular arginase inhibitor the flank organs of each of a group of hamsters are depilated by applying a thioglycolate based chemical depilatory (Surgex). To one organ of each animal 10 µl of vehicle alone once a day is applied, while to the other organ of each animal an equal amount of vehicle containing an arginase inhibitor is applied. After thirteen applications (one application per day for five days a week), the flank organs are shaved and the amount of recovered hair (hair mass) from each is weighed. Percent-reduction of hair growth is calculated by subtracting the hair mass (mg) value of the test compound treated side from the hair mass value of the vehicle treated side; the delta value obtained is then divided by the hair mass value of the vehicle treated side, and the resultant number is multiplied by 100.

The above-described assay will be referred to herein as the "Golden Syrian hamster" assay. Preferred compositions provide a reduction in hair growth of at least about 30%, more preferably at least about 45%, and most preferably at least about 60% when tested in the Golden Syrian hamster assay. A number of compositions were tested in the Golden Syrian hamster assay; the results are provided in Table I.

TABLE I

Reduction of Hair Growth by Topical Application of Inhibitors of Arginase

| Compound | Dose | Vehicle | pH | Treated (mg) | Control (mg) | Percent Inhibition (mean ± SEM) |
|---|---|---|---|---|---|---|
| α-Aminoisobutyric acid | 10% | $H_2O$ | | 1.96 ± 2.1 | 3.14 ± .26 | 34 ± 9 |
| 1-Ethyl-3-(3-dimethylaminopropyl)-carbodiimide | 10% | A | 6.5 | 0.9 ± 0.9 | 2.1 ± .21 | 57 ± 5 |
| N-Tosyl-L-arginine | 7.5% | A | 3.5 | 0.83 ± .13 | 1.62 ± .17 | 42 ± 13 |
| Octopine | 10% | B | 7.0 | 0.45 ± .07 | 1.7 ± .3 | 68 ± 6 |
| $N^G$-Hydroxy-L-arginine | 10% | A | | 0.97 ± .19 | 2.8 ± .16 | 66 ± 6 |
| N-p-Tosyl-L-arginine methyl ester | 10% | A | 7.0 | 1.24 ± .34 | 1.94 ± .4 | 34 ± 7.8 |

Vehicle A: Pure water (68%), ethanol (16%), propylene glycol (5%), dipropylene gylcol (5%), benzyl alcohol (4%), and propylene carbonate (2%).
Vehicle B: Pure water (84%), ethanol (8%), propylene glycol (2.5%), dipropylene gylcol (2.5%), benzyl alcohol (2%), and propylene carbonate (1%).

In vitro studies on inhibition of hair follicle arginase confirmed the biochemical action of the hair growth inhibitory compounds which were selected as inhibitors of hair follicle arginase. Extracts of hair follicles were obtained by excising and sonicating hair follicles obtained from hamster flank organs. The hair follicles from the hamster flank organ were excised and sonicated in a 0.01M Tris-buffered solution, pH 7.5. The sonicated extracts were centrifuged at 12,000×g, and the supernatant was used to measure arginase activity. Final reaction volumes were achieved by using 90 µl of the follicle supernatant, which was mixed with 100 µl of the Tris buffer (with or without the inhibitor), and 10 µl of 20 mM arginine incubated for 5 minutes at 37° C. The enzyme reaction was stopped by separating the enzyme from the substrate with a 10,000 molecular weight cut off filter. The product formed, ornithine, was separated from the substrate arginine using reverse phase HPLC methodology. An aliquot of the reaction was used to generate 20 µl of the filtrate which was reacted with 20 µl of O-pthalaldehyde (OPA) reagent. This reagent rapidly reacts with all primary amino acids to form fluorescent adducts that are separated on a C18 column (15 cm×3.9 mm). The 40 µl of derivatized sample is injected into the HPLC column and eluted with a stepwise gradient starting at 100% Buffer A (0.024M sodium acetate, 0.024M sodium phosphate, pH 4.0/methanol/tetrahydrofuran in a ratio of 81:15:4) and ending in a 50/50 mixture of Buffer A and Buffer B (methanol/water/tetrahydrofuran in a ratio of 75:15:10). A fluorescent detector was used to monitor the amino acid peaks as they eluted off the column. Using this method arginine eluted off the column at 20 minutes and ornithine formation when included at a final concentration of 10 uM. The magnitude of hair mass inhibition correlated well with in vitro results. N-tosyl-L-arginine methyester did not demonstrate in vitro activity but in vivo it is converted to N-tosyl-L-arginine by tissue esterases. The results are provided in Table II.

TABLE II

In Vitro Assay for Inhibitors of Hair Follicle Arginase

| Compound (10 µM) | % Inhibition |
|---|---|
| α-Aminoisobutyric acid | 27% |
| 1-ethyl-3-(3-dimethylaminopropyl)-carbodiimide | 64% |
| N-Tosyl-L-arginine | 64% |
| N-p-Tosyl-L-arginine methyl ester | 0% |
| Octopine | 50% |
| $N^G$-Hydroxy-L-arginine | 98% |

It will be appreciated by those skilled in the art that the invention can be performed within a wide range of equivalent parameters of composition and conditions without departing from the spirit or scope of the invention or of any embodiment thereof.

We claim:

1. A method of reducing mammalian hair growth, comprising
   selecting an area of skin from which reduced hair growth is desired; and
   applying to said area of skin a dermatologically acceptable composition comprising an inhibitor of arginase in an amount effective to reduce hair growth.

2. The method of claim 1, wherein said inhibitor of arginase comprises alpha aminoisobutyric acid.

3. The method of claim 1, wherein said inhibitor of arginase comprises $N^G$-hydroxy-L-arginine.

4. The method of claim 1, wherein said inhibitor of arginase comprises 1-ethyl-3-(3-dimethylaminopropyl-carbodiimide.

5. The method of claim 1, wherein said inhibitor of arginase comprises octopine.

6. The method of claim 1, wherein said inhibitor of arginase comprises N-tosyl-L-arginine.

7. The method of claim 1, wherein the concentration of said inhibitor of arginase in said composition is between 1% and 30%.

8. The method of claim 1, wherein the composition is applied to the skin in an amount of from 100 to 3000 micrograms of said inhibitor of arginase per square centimeter of skin.

9. The method of claim 1, wherein the composition is applied to the skin on the face of said mammal.

10. The method of claim 1, wherein the composition provides a reduction in hair growth of at least 30% when tested in the Golden Syrian hamster assay.

11. The method of claim 1, wherein the composition provides a reduction in hair growth of at least 45% when tested in the Golden Syrian hamster assay.

12. The method of claim 1, wherein the composition provides a reduction in hair growth of at least 60% when tested in the Golden Syrian hamster assay.

13. The method of claim 1, wherein said mammal is a human.

14. The method of claim 1, wherein said area of skin comprises an area suffering from hirsutism.

15. The method of claim 1, wherein said composition further comprises a non-toxic, dermatologically acceptable carrier or vehicle.

16. The method of claim 1, wherein said inhibitor of arginase comprises a compound which itself inhibits arginase.

17. The method of claim 1, wherein said inhibitor of arginase comprises a compound which converts in vivo to a compound which inhibits arginase when applied topically to skin.

* * * * *